United States Patent
Torchilin et al.

(10) Patent No.: US 9,238,811 B2
(45) Date of Patent: Jan. 19, 2016

(54) SIRNA PHOSPHOLIPID CONJUGATE

(75) Inventors: Vladimir Torchilin, Charlestown, MA (US); Tiziana Musacchio, Boston, MA (US)

(73) Assignee: Northeastern University, Boston, MA (US)

(*) Notice: Subject to any disclaimer, the term of this patent is extended or adjusted under 35 U.S.C. 154(b) by 7 days.

(21) Appl. No.: 13/384,057

(22) PCT Filed: Jul. 14, 2010

(86) PCT No.: PCT/US2010/041975
§ 371 (c)(1),
(2), (4) Date: Mar. 26, 2012

(87) PCT Pub. No.: WO2011/008857
PCT Pub. Date: Jan. 20, 2011

(65) Prior Publication Data
US 2012/0177723 A1    Jul. 12, 2012

Related U.S. Application Data

(60) Provisional application No. 61/225,298, filed on Jul. 14, 2009.

(51) Int. Cl.
*A61K 9/127* (2006.01)
*A61K 31/713* (2006.01)
*C07H 21/02* (2006.01)
*C12N 5/071* (2010.01)
*C12N 15/11* (2006.01)
*C12N 15/113* (2010.01)

(52) U.S. Cl.
CPC ............ *C12N 15/111* (2013.01); *C12N 15/113* (2013.01); *C12N 2310/14* (2013.01); *C12N 2310/3515* (2013.01); *C12N 2320/32* (2013.01)

(58) Field of Classification Search
USPC ....................................................... 424/450
See application file for complete search history.

(56) References Cited

U.S. PATENT DOCUMENTS

2006/0275371 A1* 12/2006 Dai et al. .................. 424/489
2008/0311040 A1* 12/2008 Berry et al. ................ 424/9.1
2010/0112619 A1* 5/2010 Graham et al. ............. 435/18

FOREIGN PATENT DOCUMENTS

WO    WO-2009-009025    *    1/2009

OTHER PUBLICATIONS

Musacchio T, Effective stabilization and delivery of siRNA: reversible siRNA-phospholipid conjugate in nanosized mixed polymeric micelles, 2010, ACS, Bioconjugate Chemistry, 21, 1530-1536.*
Navarro G, Phospholipid-polyethylenimine conjugate-based micelle-like nanoparticles for siRNA delivery, Drug Deliv Trans Res, 2011, 1(1), 25-33.*
Elbashir, et al., "Duplexes of 21-Nucleotide RNAs Mediate RNA Interference in Cultured Mammalian Cells," *Nature*, vol. 411, pp. 494-498 (May 24, 2001).
Hamilton, et al., "A Species of Small Antisense RNA in Post-transcriptional Gene Silencing in Plants," *Science*, vol. 286, pp. 950-952 (Oct. 29, 1999).
International Search Report and Written Opinion issued by the U.S. Patent and Trademark Office as the International Searching Authority for International Application No. PCT/US10/041975 mailed Oct. 25, 2010 (6 pgs.).
Meng, et al., "Reduction-Sensitive Polymers and Bioconjugates for Biomedical Applications," *Biomaterials*, vol. 30, pp. 2180-2198 (Feb. 2009).
Novina, et al., "The RNAi Revolution," *Nature*, vol. 430, pp. 161-164 (2004).

* cited by examiner

*Primary Examiner* — Frederick Krass
*Assistant Examiner* — Celeste A Roney
(74) *Attorney, Agent, or Firm* — Wilmer Cutler Pickering Hale and Dorr LLP

(57) ABSTRACT siRNA-conjugated liposomes and micelles, methods of making such conjugates, and methods of using such conjugates, such as for the delivery of siRNA to cells to reduce expression of target polypeptides in such cells, are described.

10 Claims, 6 Drawing Sheets

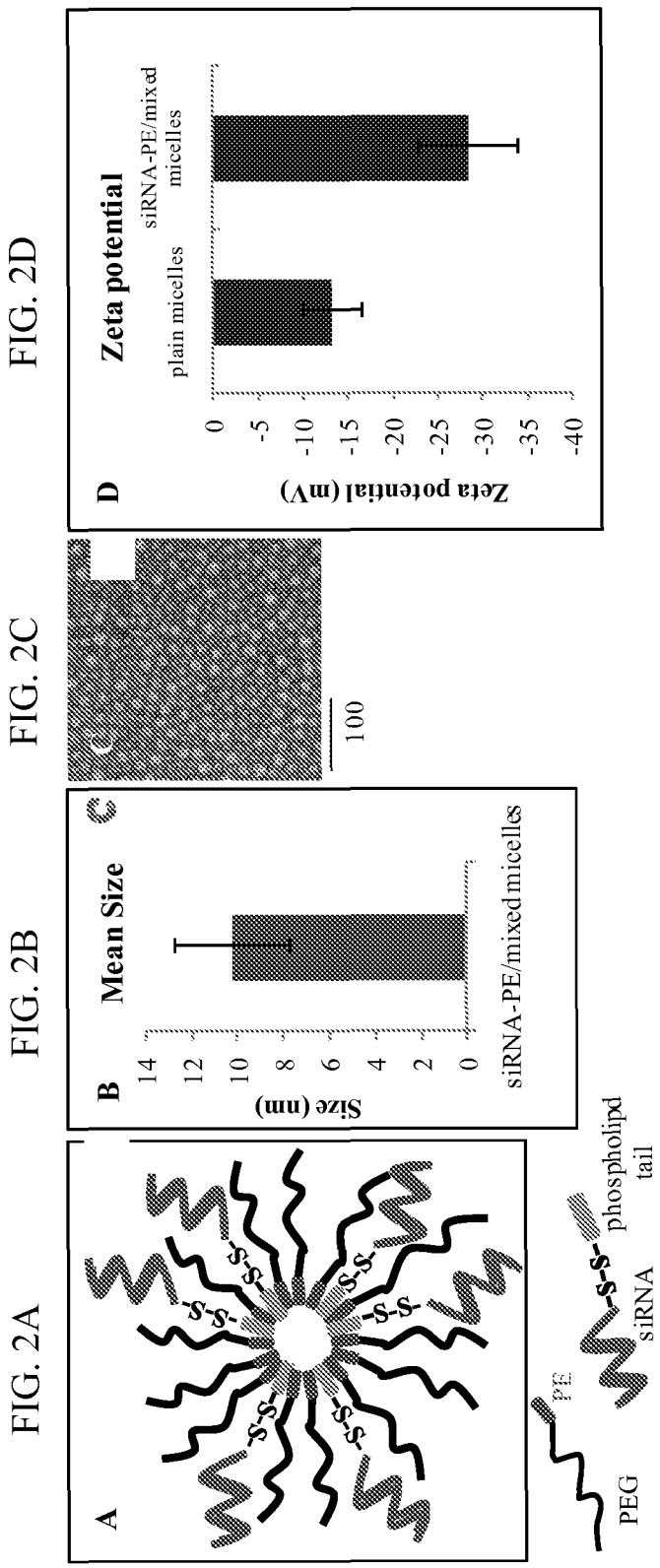

SIRNA PHOSPHOLIPID CONJUGATE

CROSS REFERENCE TO RELATED APPLICATIONS

This application is a National Stage Entry of PCT/US10/41975, filed Jul. 14, 2010, which claims the benefit of U.S. Provisional Application No. 61/225,298, filed Jul. 14, 2009, the entire contents of which are hereby incorporated by reference herein.

FIELD OF THE INVENTION

This disclosure is in the fields of molecular biology and medicine. More specifically, this disclosure relates to siRNA control of gene expression.

BACKGROUND

Small interfering RNA (siRNA) is a short double stranded RNA. It behaves like a mediator of the RNA interference phenomenon silencing the specific gene expression by triggering the cleavage of a target messenger RNA (mRNA) at post-transcriptional level in the cytoplasm (Hamilton, et al., Science 1999; Elbashir, et al., Nature (2001)). siRNA is a powerful tool to control cellular processes at a post-transcriptional level. Its great potency is due to the high sequence-specific inhibition efficiency (Novina et al., Nature (2004) 430:161-164). Thus, siRNA strategy has been strongly considered for the down-regulation of certain proteins in the areas of functional genomics and genomic therapeutics.

Although siRNA has been used as a therapeutic agent for various genetic diseases, its therapeutic application is still limited because of its instability against nucleases. Thus, what is needed are siRNA molecules that are more stable, and thus more active and useful as therapeutic agents.

SUMMARY

The invention is based, in part, on the discovery that siRNA can be reversibly conjugated to a phospholipid, such as a phospholipid within a liposome or a micelle, and the siRNA can be unconjugated upon exposure to reducing conditions, such as inside a cell.

Accordingly, in one aspect, the disclosure features a conjugated siRNA composition comprising a micelle or a liposome, the micelle or the liposome comprising phospholipids; and an siRNA reversibly conjugated to a first phospholipid of the micelle or the liposome.

In some embodiments, the siRNA is reversibly conjugated to the first phospholipid by a disulfide bond. In certain embodiments, the siRNA is unconjugated from the first phospholipid upon exposure to reducing conditions.

In certain embodiments, the siRNA reversibly conjugated to the first phospholipid has increased stability relative to the same siRNA not conjugated to the first phospholipid. In particular embodiments, the siRNA reversibly conjugated to the first phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, more stable than the same siRNA not conjugated to the first phospholipid.

In some embodiments, the siRNA reversibly conjugated to the first phospholipid exhibits reduced degradation by RNase relative to the same siRNA not conjugated to the first phospholipid. In particular embodiments, the level of degradation by RNase is reduced by about 10%, by about 20%, by about 30%, by about 40%, by about 50%, by about 60%, by about 70%, by about 80%, by about 90%, by about 95%, or by about 100%, relative to the same siRNA not conjugated to the first phospholipid.

In certain embodiments, the siRNA reversibly conjugated to the first phospholipid exhibits an increased half-life when administered into a subject, relative to the same siRNA not conjugated to the first phospholipid. In particular embodiments, the increase in half-life of the siRNA reversibly conjugated to the first phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, relative to the same siRNA not conjugated to the first phospholipid. In particular embodiments, the half-life of the siRNA reversibly conjugated to the first phospholipid exhibits a half-life, when administered into a subject, of about 6 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or longer.

In some embodiments, about 1% to about 100% of the phospholipids of the liposome or the micelle are reversibly conjugated to the siRNA. In other embodiments, about 1%, about 5%, about 10%, about 20%, about 30%, about 40%, about 50%, about 60%, about 70%, about 80%, about 90%, or about 100% of the phospholipids of the liposome or the micelle are reversibly conjugated to the siRNA.

In some embodiments, the siRNA comprises about 0.5% to about 90% of the liposome or the micelle by weight. In particular embodiments, the siRNA comprises about 0.5%, about 1%, about 5%, about 10%, about 20%, about 30%, about 40%, about 50%, about 60%, about 70%, about 80%, or about 90% of the liposome or micelle by weight.

In some embodiments, the micelle or the liposome further comprises polyethylene glycol (PEG) conjugated to a second phospholipid of the micelle or the liposome. In certain embodiments, the first phospholipid and the second phospholipid are different. In other embodiments, the first phospholipid and the second phospholipid are the same. In some embodiments, the first phospholipid is phosphatidylcholine (PC), phosphatidylglycerol (PG), phosphatidylinositol (PI), phosphatidic acid (PA), phosphatidyethanolamine (PE), phosphatidylserine (PS), or phosphoethanolamine.

In some embodiments, about 50% of the phospholipids are reversibly conjugated to the siRNA and about 50% of the phospholipids are conjugated to PEG, about 40% of the phospholipids are reversibly conjugated to the siRNA and about 60% of the phospholipids are conjugated to PEG, about 30% of the phospholipids are reversibly conjugated to the siRNA and about 70% of the phospholipids are conjugated to PEG, about 20% of the phospholipids are reversibly conjugated to the siRNA and about 80% of the phospholipids are conjugated to PEG, about 10% of the phospholipids are reversibly conjugated to the siRNA and about 90% of the phospholipids are conjugated to PEG, about 60% of the phospholipids are reversibly conjugated to the siRNA and about 40% of the phospholipids are conjugated to PEG, about 70% of the phospholipids are reversibly conjugated to the siRNA and about 30% of the phospholipids are conjugated to PEG, about 80% of the phospholipids are reversibly conjugated to the siRNA and about 20% of the phospholipids are conjugated to PEG, or about 90% of the phospholipids are reversibly conjugated to the siRNA and about 10% of the phospholipids are conjugated to PEG.

In certain embodiments, the micelle or the liposome comprises a wt/wt ratio of (phospholipids reversibly conjugated to the siRNA) to (phospholipids conjugated to PEG) of about 1:10 to about 1:5000, about 1:50 to about 1:2500, about 1:100 to about 1:2000, about 1:150 to about 1:1500, about 1:200 to about 1:1000; about 1:250 to about 1:900, about 1:300 to about 1:800, about 1:400 to about 1:750, or about 1:500 to about 600.

In some embodiments, the composition further comprises a targeting agent conjugated to a phospholipid of the micelle or liposome. In some embodiments, the targeting agent is conjugated to the first phospholipid. In other embodiments, the targeting agent is conjugated to the second phospholipid. In yet other embodiments, the targeting agent is conjugated to both the first and the second phospholipid. In still other embodiments, the targeting agent is conjugated to a phospholipid not conjugated to the siRNA or the PEG.

In another aspect, the disclosure features an siRNA composition comprising an siRNA reversibly conjugated to a phospholipid. In some embodiments, the siRNA is reversibly conjugated to the phospholipid by a disulfide bond. In certain embodiments, the siRNA is unconjugated from the phospholipid upon exposure to reducing conditions.

In certain embodiments, the phospholipid is phosphatidylcholine (PC), phosphatidylglycerol (PG), phosphatidylinositol (PI), phosphatidic acid (PA), phosphatidyethanolamine (PE), phosphatidylserine (PS), or phosphoethanolamine.

In particular embodiments, the siRNA reversibly conjugated to the phospholipid has increased stability relative to the same siRNA not conjugated to the phospholipid. In certain embodiments, the siRNA reversibly conjugated to the phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, more stable than the same siRNA not conjugated to the phospholipid.

In some embodiments, the siRNA reversibly conjugated to the phospholipid exhibits reduced degradation by RNase relative to the same siRNA not conjugated to the phospholipid. In particular embodiments, the level of degradation by RNase is reduced by about 10%, by about 20%, by about 30%, by about 40%, by about 50%, by about 60%, by about 70%, by about 80%, by about 90%, by about 95%, or by about 100%, relative to the same siRNA not conjugated to the phospholipid.

In certain embodiments, the siRNA reversibly conjugated to the phospholipid exhibits an increased half-life when administered into a subject, relative to the same siRNA not conjugated to the phospholipid. In particular embodiments, the increase in half-life of the siRNA reversibly conjugated to the phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, relative to the same siRNA not conjugated to the phospholipid. In particular embodiments, the half-life of the siRNA reversibly conjugated to the phospholipid exhibits a half-life, when administered into a subject, of about 6 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or longer.

In another aspect, the disclosure features a method of inhibiting expression of a target polypeptide in a subject, the method comprising administering to the subject a conjugated siRNA composition in an amount sufficient to inhibit expression of the target polypeptide in a cell of the subject, wherein the conjugated siRNA composition comprises (i) a micelle or a liposome, the micelle or the liposome comprising phospholipids; and (ii) an siRNA reversibly conjugated to a first phospholipid of the micelle or the liposome; and allowing the siRNA to unconjugate from the first phospholipid of the micelle or the liposome within the cell of the subject, thereby inhibiting the expression of the target polypeptide in the subject.

In some embodiments, the siRNA is reversibly conjugated to the first phospholipid by a disulfide bond. In certain embodiments, the siRNA is unconjugated from the first phospholipid upon exposure to reducing conditions within the cell.

In particular embodiments, the expression of the target polypeptide is reduced by about 10%, about 20%, about 30%, about 40%, about 50%, about 60%, about 70%, about 80%, about 90%, or about 100%, relative to the expression of the target polypeptide in the absence of administration of the conjugated siRNA composition.

In certain embodiments, the siRNA reversibly conjugated to the first phospholipid has increased stability relative to the same siRNA not conjugated to the first phospholipid. In some embodiments, the siRNA reversibly conjugated to the first phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, more stable than the same siRNA not conjugated to the first phospholipid.

In some embodiments, the siRNA reversibly conjugated to the first phospholipid exhibits reduced degradation by RNase relative to the same siRNA not conjugated to the first phospholipid. In particular embodiments, the level of degradation by RNase is reduced by about 10%, by about 20%, by about 30%, by about 40%, by about 50%, by about 60%, by about 70%, by about 80%, by about 90%, by about 95%, or by about 100%, relative to the same siRNA not conjugated to the first phospholipid.

In certain cases, the siRNA reversibly conjugated to the first phospholipid may exhibit an increased half-life when administered to the subject, relative to the same siRNA not conjugated to the first phospholipid. In some embodiments, the increase in half-life of the siRNA reversibly conjugated to the first phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, relative to the same siRNA not conjugated to the first phospholipid. In particular embodiments, the half-life of the siRNA reversibly conjugated to the first phospholipid exhibits a half-life, when administered into the subject, of about 6 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or longer.

In some embodiments, about 1% to about 100% of the phospholipids of the liposome or the micelle are reversibly conjugated to the siRNA. In other embodiments, about 1%, about 5%, about 10%, about 20%, about 30%, about 40%, about 50%, about 60%, about 70%, about 80%, about 90%, or about 100% of the phospholipids of the liposome or the micelle are reversibly conjugated to the siRNA.

In certain embodiments, the siRNA comprises about 0.5% to about 90% of the liposome or the micelle by weight. In particular embodiments, the siRNA comprises about 0.5%, about 1%, about 5%, about 10%, about 20%, about 30%, about 40%, about 50%, about 60%, about 70%, about 80%, or about 90% of the liposome or micelle by weight.

In some embodiments, the micelle or the liposome further comprises polyethylene glycol (PEG) conjugated to a second phospholipid of the micelle or the liposome. In certain embodiments, the first phospholipid and the second phospholipid are different. In other embodiments, the first phospholipid and the second phospholipid are the same. In some embodiments, the first phospholipid is phosphatidylcholine (PC), phosphatidylglycerol (PG), phosphatidylinositol (PI), phosphatidic acid (PA), phosphatidyethanolamine (PE), phosphatidylserine (PS), or phosphoethanolamine.

In some embodiments, about 50% of the phospholipids are reversibly conjugated to the siRNA and about 50% of the phospholipids are conjugated to PEG, about 40% of the phospholipids are reversibly conjugated to the siRNA and about 60% of the phospholipids are conjugated to PEG, about 30% of the phospholipids are reversibly conjugated to the siRNA and about 70% of the phospholipids are conjugated to PEG, about 20% of the phospholipids are reversibly conjugated to the siRNA and about 80% of the phospholipids are conjugated to PEG, about 10% of the phospholipids are reversibly conjugated to the siRNA and about 90% of the phospholipids are conjugated to PEG, about 60% of the phospholipids are reversibly conjugated to the siRNA and about 40% of the phospholipids are conjugated to PEG, about 70% of the phospholipids are reversibly conjugated to the siRNA and about 30% of the phospholipids are conjugated to PEG, about 80% of the phospholipids are reversibly conjugated to the siRNA and about 20% of the phospholipids are conjugated to PEG, or about 90% of the phospholipids are reversibly conjugated to the siRNA and about 10% of the phospholipids are conjugated to PEG.

In particular embodiments, the micelle or the liposome comprises a wt/wt ratio of (phospholipids reversibly conjugated to the siRNA) to (phospholipids conjugated to PEG) of about 1:10 to about 1:5000, about 1:50 to about 1:2500, about 1:100 to about 1:2000, about 1:150 to about 1:1500, about 1:200 to about 1:1000; about 1:250 to about 1:900, about 1:300 to about 1:800, about 1:400 to about 1:750, or about 1:500 to about 600.

In certain embodiments, the conjugated siRNA composition further comprises a targeting agent conjugated to a phospholipid of the micelle or the liposome. In some embodiments, the targeting agent mediates uptake of the conjugated siRNA composition by the cell. In some embodiments, the targeting agent is conjugated to the first phospholipid. In other embodiments, the targeting agent is conjugated to the second phospholipid. In yet other embodiments, the targeting agent is conjugated to both the first and the second phospholipid. In yet other embodiments, the targeting agent is conjugated to a phospholipid not conjugated to the siRNA or the PEG.

In certain embodiments, the subject is a human, ape, monkey, orangutan, chimpanzee, dog, cat, guinea pig, rabbit, rat, mouse, horse, cattle, or cow.

In another aspect, the disclosure features a method of inhibiting expression of a target polypeptide in a cell, the method comprising delivering into a cell a conjugated siRNA composition in an amount sufficient to inhibit expression of the target polypeptide in the cell, wherein the conjugated siRNA composition comprises (i) a micelle or a liposome, the micelle or the liposome comprising phospholipids; and (ii) an siRNA reversibly conjugated to a first phospholipid of the micelle or the liposome; and allowing the siRNA to unconjugate from the first phospholipid of the micelle or the liposome within the cell, thereby inhibiting the expression of the target polypeptide in the cell.

In some embodiments, the siRNA is reversibly conjugated to the first phospholipid by a disulfide bond. In certain embodiments, the siRNA is unconjugated from the first phospholipid upon exposure to reducing conditions within the cell.

In particular embodiments, the expression of the target polypeptide is reduced by about 10%, about 20%, about 30%, about 40%, about 50%, about 60%, about 70%, about 80%, about 90%, or about 100%, relative to the expression of the target polypeptide in the absence of administration of the conjugated siRNA composition.

In some embodiments, the siRNA reversibly conjugated to the first phospholipid has increased stability relative to the same siRNA not conjugated to the first phospholipid. In certain embodiments, the siRNA reversibly conjugated to the first phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, more stable than the same siRNA not conjugated to the first phospholipid.

In certain embodiments, the siRNA reversibly conjugated to the first phospholipid exhibits reduced degradation by RNase relative to the same siRNA not conjugated to the first phospholipid. In particular embodiments, the level of degradation by RNase is reduced by about 10%, by about 20%, by about 30%, by about 40%, by about 50%, by about 60%, by about 70%, by about 80%, by about 90%, by about 95%, or by about 100%, relative to the same siRNA not conjugated to the first phospholipid.

In some embodiments, the siRNA reversibly conjugated to the first phospholipid exhibits an increased half-life when administered to a subject, relative to the same siRNA not conjugated to the first phospholipid. In certain embodiments, the increase in half-life of the siRNA reversibly conjugated to the first phospholipid is about 10% to about 10000%, about 20% to about 1000%, about 30% to about 500%, about 40% to about 400%, about 50% to about 300%, about 60% to about 200%, about 70% to about 150%, about 80% to about 100%, about 25%, about 50%, about 75%, about 100%, about 150%, about 200%, about 250%, about 500%, about 1000%, about 1500%, about 2000%, about 2500%, about 5000%, about 10000%, about 50000%, or more, relative to the same siRNA not conjugated to the first phospholipid. In particular embodiments, the half-life of the siRNA reversibly conjugated to the first phospholipid exhibits a half-life, when administered into a subject, of about 6 hours, about 12 hours, about 24 hours, about 2 days, about 3 days, about 4 days, about 5 days, about 6 days, about 7 days, about 8 days, about 9 days, about 10 days, about 11 days, about 12 days, about 13 days, about 14 days, or longer.

In certain embodiments, about 1% to about 100% of the phospholipids of the liposome or the micelle are reversibly conjugated to the siRNA. In other embodiments, about 1%, about 5%, about 10%, about 20%, about 30%, about 40%, about 50%, about 60%, about 70%, about 80%, about 90%, or about 100% of the phospholipids of the liposome or the micelle are reversibly conjugated to the siRNA.

In some embodiments, the siRNA comprises about 0.5% to about 90% of the liposome or the micelle by weight. In particular embodiments, the siRNA comprises about 0.5%, about 1%, about 5%, about 10%, about 20%, about 30%, about 40%, about 50%, about 60%, about 70%, about 80%, or about 90% of the liposome or micelle by weight.

In particular embodiments, the micelle or the liposome further comprises polyethylene glycol (PEG) conjugated to a second phospholipid of the micelle or the liposome. In certain embodiments, the first phospholipid and the second phospholipid are different. In other embodiments, the first phospholipid and the second phospholipid are the same. In yet other embodiments, the first phospholipid is phosphatidylcholine (PC), phosphatidylglycerol (PG), phosphatidylinositol (PI), phosphatidic acid (PA), phosphatidyethanolamine (PE), phosphatidylserine (PS), or phosphoethanolamine.

In some embodiments, about 50% of the phospholipids are reversibly conjugated to the siRNA and about 50% of the phospholipids are conjugated to PEG, about 40% of the phospholipids are reversibly conjugated to the siRNA and about 60% of the phospholipids are conjugated to PEG, about 30% of the phospholipids are reversibly conjugated to the siRNA and about 70% of the phospholipids are conjugated to PEG, about 20% of the phospholipids are reversibly conjugated to the siRNA and about 80% of the phospholipids are conjugated to PEG, about 10% of the phospholipids are reversibly conjugated to the siRNA and about 90% of the phospholipids are conjugated to PEG, about 60% of the phospholipids are reversibly conjugated to the siRNA and about 40% of the phospholipids are conjugated to PEG, about 70% of the phospholipids are reversibly conjugated to the siRNA and about 30% of the phospholipids are conjugated to PEG, about 80% of the phospholipids are reversibly conjugated to the siRNA and about 20% of the phospholipids are conjugated to PEG, or about 90% of the phospholipids are reversibly conjugated to the siRNA and about 10% of the phospholipids are conjugated to PEG.

In certain embodiments, the micelle or the liposome comprises a wt/wt ratio of (phospholipids reversibly conjugated to the siRNA) to (phospholipids conjugated to PEG) of about 1:10 to about 1:5000, about 1:50 to about 1:2500, about 1:100 to about 1:2000, about 1:150 to about 1:1500, about 1:200 to about 1:1000; about 1:250 to about 1:900, about 1:300 to about 1:800, about 1:400 to about 1:750, or about 1:500 to about 600.

In particular embodiments, the conjugated siRNA composition further comprises a targeting agent conjugated to a phospholipid of the micelle or the liposome. In some embodiments, the targeting agent mediates uptake of the conjugated siRNA composition by the cell. In certain embodiments, the targeting agent is conjugated to the first phospholipid. In other embodiments, the targeting agent is conjugated to the second phospholipid. In yet other embodiments, the targeting agent is conjugated to both the first and the second phospholipid. In other embodiments, the targeting agent is conjugated to a phospholipid not conjugated to the siRNA or the PEG. In some embodiments, the targeting agent mediates delivery into the cell.

In certain embodiments, the cell is within a subject. In some embodiments, the subject is a human, ape, monkey, orangutan, chimpanzee, dog, cat, guinea pig, rabbit, rat, mouse, horse, cattle, or cow.

The following figures are presented for the purpose of illustration only, and are not intended to be limiting.

BRIEF DESCRIPTION OF THE FIGURES

FIG. 2A is a schematic representation of a siRNA-S-S-PE/PEG-PE mixed micelle.

FIG. 2B is a graphic representation of mean size of mixed micelle formulations.

FIG. 2C is a representation of a transmission electron micrograph showing the morphology and size distribution of 1:750 (wt/wt) siRNA-PE/PEG-PE micelles.

FIG. 2D is a graphic representation of the mean zeta potential value of siRNA-S-S-PE/PEG-PE mixed micelle formulations and plain PEG-PE micelles.

DESCRIPTION

Figures 1A, 1B:
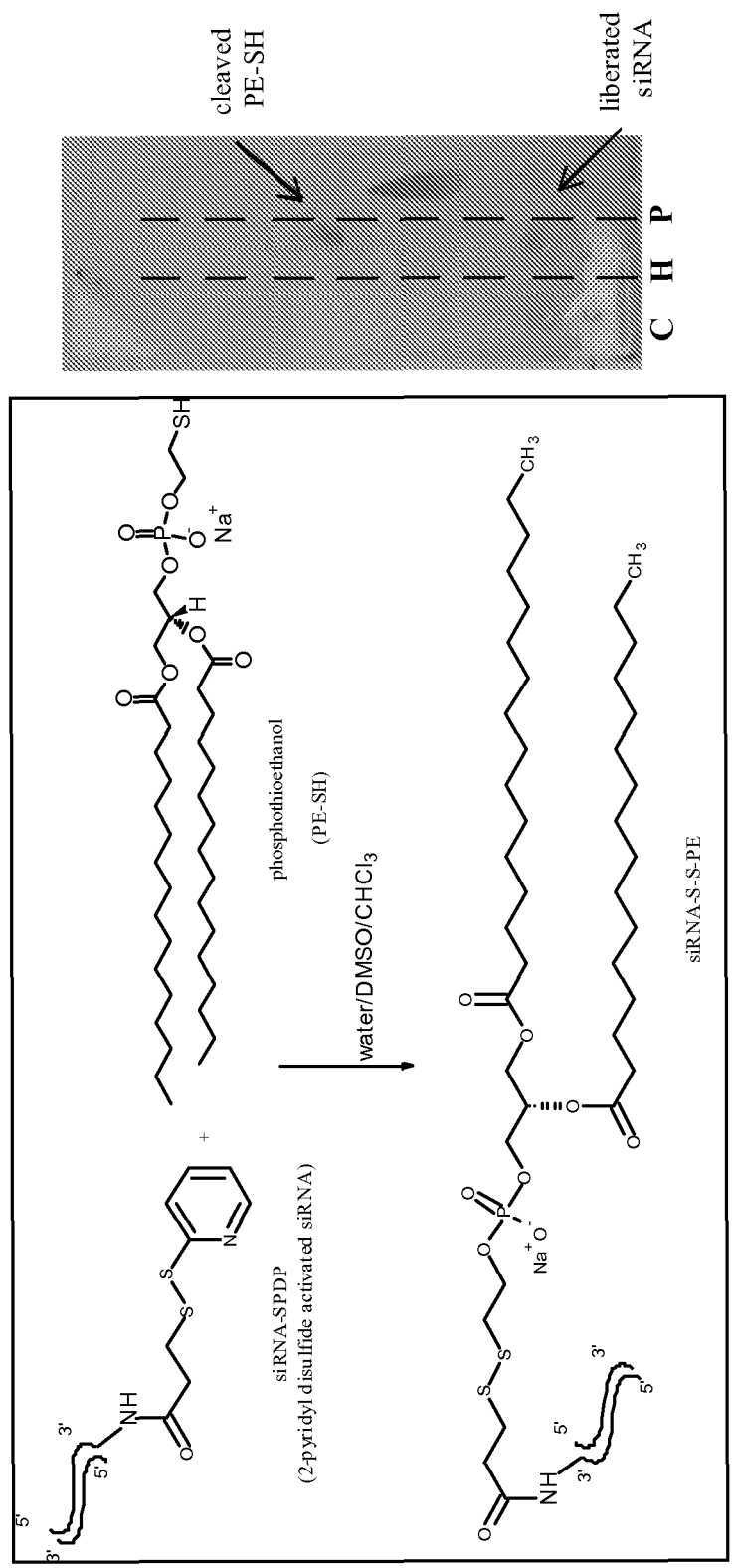
FIG. 1A is a schematic representation of the synthesis of siRNA-S-S-PE.
FIG. 1B is a photographic representation of the cleavage of disulfide bonds in a 10 mM glutathione solution as monitored by TLC, where "C" represents siRNA-S-S-PE before hydrolysis; "H" represents siRNA after the hydrolysis of siRNA-conjugate; and "P" represents free phospholipid.

All publications, patent applications, patents, and other references mentioned herein are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DEFINITIONS

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "about" is used herein to mean a value – or +20% of a given numerical value. Thus, "about 60%" means a value of between 60–(20% of 60) and 60+(20% of 60) (i.e., between 48 and 70).

The terms "peptide", "polypeptide" and "protein" are used interchangeably herein.

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

The term "treatment" or "treating", as used herein, refers to administering a therapy in an amount, manner, and/or mode effective to improve a condition, symptom, or parameter associated with a disorder or condition or to prevent or reduce progression of a disorder or condition, either to a statistically significant degree or to a degree detectable to one skilled in the art. An effective amount, manner, or mode can vary depending on the subject and may be tailored to the subject.

The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda. In one embodiment, the antibody is glycosylated.

As used herein, the terms "coupled", "linked", "fused", and "fusion" are used interchangeably. These terms refer to the joining together of two more elements or components by whatever means, including chemical conjugation or recombinant means.

An "RNA interfering agent", as used herein, is defined as any agent that interferes with or inhibits expression of a target gene or genomic sequence by RNA interference (RNAi). Such RNA interfering agents include, but are not limited to, nucleic acid molecules including RNA molecules that are homologous to the target gene or genomic sequence, or a fragment thereof, short interfering RNA (siRNA), and small molecules that interfere with or inhibit expression of a target gene by RNA interference (RNAi).

"RNA interference" or "RNAi", as used herein, is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes.

"Short interfering RNA", "small interfering RNA" or "siRNA", as used herein, is an agent that functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, of about 15 to about 28 nucleotides, of about 19 to about 25 nucleotides in length, or about 19, 20, 21, or 22 nucleotides in length, and can contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. The siRNA is capable of promoting RNA interference, e.g., through degradation or specific post-transcriptional gene silencing (PTGS) of the target messenger RNA (mRNA).

As used herein, "inhibition of target gene expression" includes any decrease in expression or protein activity or level of the target gene or protein encoded by the target gene. The decrease can be of at least about 30%, 40%, 50%, 60%, 70%, 80%, 90%, 95% or 99% or more, as compared to the expression of a target gene or the activity or level of the protein encoded by a target gene that has not been targeted by an RNA interfering agent.

General

The disclosure is based, in part, on the discovery that an siRNA reversibly conjugated to a phospholipid of a micelle can be released from the phospholipid when exposed to reducing conditions, and the released siRNA can inhibit expression of a target polypeptide. While not wishing to be bound by theory, it is believed that the conjugated siRNA compositions described herein have increased stability relative to the siRNA when not reversibly conjugated to a phospholipid. For example, siRNA, when incorporated into a conjugated siRNA composition described herein, can be protected from degradation (e.g., enzymes such as RNase) and can have higher circulation times when administered into a subject. Liposomes and micelles containing the reversibly conjugated siRNA are useful for the delivery of siRNA to target cells and tissues to reduce or inhibit the expression of a target polypeptide, e.g., to treat a disease or a disorder.

siRNA

The present disclosure relates to siRNA molecules of about 15 to about 40, about 20 to about 40, or about 15 to about 28 nucleotides in length, which are homologous to a target gene or sequence and mediate RNAi of the target gene or sequence. The siRNA molecules can have a length of about 19 to about 25 nucleotides, such as a length of about 19, 20, 21, or 22 nucleotides. The siRNA molecules can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In some instances, at least one strand of the RNA molecule has a 3' overhang from about 0 to about 6 nucleotides (e.g., pyrimidine nucleotides, purine nucleotides) in length. In other situations, the 3' overhang is from about 1 to about 5 nucleotides, from about 1 to about 3 nucleotides, from about 2 to about 4 nucleotides, from about 3 to about 6 nucleotides, or from about 2 to about 5 nucleotides in length. In one instance, the RNA molecule is double-stranded, one strand has a 3' overhang and the other strand can be blunt-ended or have an overhang. When the RNA molecule is double stranded and both strands comprise an overhang, the length of the overhangs can be the same or different for each strand. In a particular instance, the RNA comprises about 19, 20, 21, or 22 nucleotide strands that are paired and that have overhangs of from about 1 to about 3, particularly about 2, nucleotides on both 3' ends of the RNA. The 3' overhangs can be stabilized against degradation. In some instances, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs, by 2'-deoxythymidine can be used.

siRNA molecules useful in the methods described herein are not limited to those molecules containing only RNA, but can also encompass chemically modified nucleotides and non-nucleotides, and also include molecules wherein a ribose sugar molecule is substituted for another sugar molecule or a molecule which performs a similar function. Moreover, a non-natural linkage between nucleotide residues may be used, such as a phosphorothioate, phosphorodithioate, alkylphosphonate, phosphoramidate, carbamate, phosphatetriester, alkylphosphonothioate, and/or acetamidate linkage. The RNA strand can be derivatized with a reactive functional group of a reporter group, such as a fluorophore. Particularly useful derivatives are modified at a terminus or termini of an RNA strand, such as the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'-O-substituted moieties (such as 2'O-alkylated residues or 2'-O-methyl ribosyl derivatives and 2'-O-fluoro ribosyl derivatives).

The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue.

The target gene can be a gene or sequence of a cellular gene, viral gene, or infectious gene, or a fragment thereof. An siRNA can be substantially homologous to the target gene or genomic sequence, or a fragment thereof. As used herein, the term "homologous" is defined as being substantially identical, sufficiently complementary, or similar to the target mRNA, or a fragment thereof, to effect RNA interference of the target. Non-natural bases that yield successful inhibition can also be incorporated.

Synthetic siRNA molecules can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir et al., *Nature* 411:494-498 (2001); Elbashir et al., *Genes & Development* 15:188-200 (2001); Harborth et al., *J. Cell Science* 114:4557-4565 (2001); Masters et al., *Proc. Natl. Acad. Sci.* (*USA*) 98:8012-8017 (2001); and Tuschl et al., *Genes & Development* 13:3191-3197 (1999)). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not difficult to synthesize and are readily provided in a quality suitable for RNAi.

The targeted region of an siRNA molecule can be selected from a given target gene sequence, e.g., a cellular or viral target sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule involves identifying the 23 nucleotide sequence motif AA(N19)TT (where N can be any nucleotide) and selecting sequences with at least 25%, 30%, 35%, 40%, 45%, 50%, 55%, 60%, 65%, 70% or 75% G/C content. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs can be used so that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq, as well as commercially available oligosynthesis companies such as Oligoengine™, can also be used to select siRNA sequences against EST libraries to ensure that only one gene is targeted.

Liposomes

The present disclosure includes siRNA molecules reversibly conjugated to a phospholipid of a liposome. Upon exposure to reducing conditions, such as within a cell, the siRNA is unconjugated from the phospholipid of the liposome and can inhibit expression of a target polypeptide. Liposomes are vesicles that include one or more concentrically ordered lipid bilayer(s) encapsulating an aqueous phase, when in an aqueous environment. Such vesicles are formed in the presence of "vesicle-forming lipids", which are defined herein as amphipathic lipids capable of either forming or being incorporated into a bilayer structure. The term includes lipids that are capable of forming a bilayer by themselves or when in combination with another lipid or lipids. An amphipathic lipid is incorporated into a lipid bilayer by having its hydrophobic moiety in contact with the interior, hydrophobic region of the bilayer membrane and its polar head moiety oriented towards an outer, polar surface of the membrane. Hydrophilicity arises from the presence of functional groups, such as hydroxyl, phosphate, carboxyl, sulfate, amino or sulfhydryl groups. Hydrophobicity results from the presence of a long chain of aliphatic hydrocarbon groups.

Liposomes include multilamellar vesicles, multivesicular liposomes, unilamellar vesicles, and giant liposomes. Multilamellar liposomes (also known as multilamellar vesicles ("MLV")) contain multiple concentric bilayers within each liposome particle, resembling the layers of an onion. Multivesicular liposomes consist of lipid membranes enclosing multiple non-concentric aqueous chambers. Unilamellar liposomes enclose a single internal aqueous compartment. Single bilayer (or substantially single bilayer) liposomes include small unilamellar vesicles ("SUV") and large unilamellar vesicles ("LUV"). LUVs and SUVs can range in size from about 50 nm to about 500 nm and about 20 nm to about 50 nm, respectively. Giant liposomes can range in size from about 5000 nm to about 50,000 nm (Needham et al., *Colloids and Surfaces B: Biointerfaces* 18:183-195 (2000)).

Any suitable vesicle-forming lipid (e.g., naturally occurring lipids and synthetic lipids) can be utilized in the liposomes and micelles described herein. Suitable lipids include, without limitation, phospholipids such as phosphatidylcholine (PC), phosphatidylglycerol (PG), phosphatidylinositol (PI), phosphatidic acid (PA), phosphatidyethanolamine (PE), phosphatidylserine (PS), and phosphoethanolamine; sterols such as cholesterol; glycolipids; sphingolipids such as sphingosine, ceramides, sphingomyelin, and glycosphingolipids (such as cerebrosides and gangliosides). Particular lipids include dipalmitoyl phosphatidylcholine, cholesterol, ganglioside, dicetyl phosphate, dipalmitoyl phosphatidylethanolamine, sodium cholate, dicetyl phosphatidylethanolamine-polyglycerin 8G, dimyristoyl phosphatidylcholine, distearoyl phosphatidylcholine, dioleoyl phosphatidylcholine, dimyristoyl phosphatidylserine, dipalmitoyl phosphatidylserine, distearoyl phosphatidylserine, dioleoyl phosphatidylserine, dimyristoyl phosphatidylinositol, dipalmitoyl phosphatidylinositol, distearoyl phosphatidylinositol, dioleoyl phosphatidylinositol, dimyristoyl phosphatidylethanolamine, distearoyl phosphatidylethanolamine, distearoyl phosphoethanolamine, dioleoyl phosphatidylethanolamine, dimyristoyl phosphatidic acid, dipalmitoyl phosphatidic acid, distearoyl phosphatidic acid, dioleoyl phosphatidic acid, galactosyl ceramides, glycosyl ceramides, lactosyl ceramides, phosphatides, globosides, GM1 (Gal$\beta$1, 3GalNAc$\beta$1, 4(NeuAa2,3)Gal$\beta$1, 4Glc$\beta$1, 1'Cer), ganglioside GD1a, ganglioside GD1b, dimyristoyl phosphatidylglycerol, dipalmitoyl phosphatidylglycerol, distearoyl phosphatidylglycerol, dioleoyl phosphatidylglycerol, distearoyl-glycero-phosphoethanolamine, and 1,2-dioleoyl-sn-glycero-3-phosphoethanolamine. Suitable phospholipids can include one or two acyl chains having any number of carbon atoms, such as about 6 to about 24 carbon atoms, selected independently of one another and with varying degrees of unsaturation. Thus, combinations of phospholipid of different species and different chain lengths in varying ratios can be used. Mixtures of lipids in suitable ratios, as judged by one of skill in the art, can also be used.

Particular phospholipids useful in the methods described herein are 1,2-didecanoyl-sn-glycero-3-phosphoethanolamine, 1,2-dilauroyl-sn-glycero-3-phosphoethanolamine, 1,2-dimyristoyl-sn-glycero-3-phosphoethanolamine, 1,2-dipentadecanoyl-sn-glycero-3-phosphoethanolamine, 1,2-diphytanoyl-sn-glycero-3-phosphoethanolamine, and 1,2-distearoyl-sn-glycero-3-phosphoethanolamine.

Liposomes can be generated using a variety of techniques known in the art. These techniques include, without limitation, ether injection (Deamer et al., *Acad. Sci.* 308:250 (1978)); surfactant (Brunner et al., *Biochim. Biophys. Acta* 455:322 (1976)); Ca$^{2+}$ fusion (Paphadjopoulos et al., *Biochim. Biophys. Acta* 394:483 (1975)); freeze-thaw (Pick et al., *Arach. Biochim. Biophys.* 212:186 (1981)); reverse-phase evaporation (Szoka et al., *Biochim. Biophys. Acta* 601:559 (1980)); ultrasonic treatment (Huang et al., *Biochem.* 8:344 (1969)); ethanol injection (Kremer et al., *Biochem.* 16:3932 (1977)); extrusion (Hope et al., *Biochim. Biophys. Acta* 812: 55 (1985)); French press (Barenholz et al., *FEBS Lett.* 99:210 (1979)); thin film hydration (Bangham et al., *J. Mol. Biol.* 13:238-252 (1965)); and any other methods described herein or known in the art. Liposomes can also be generated using commercially available kits (e.g., from Boehringer-Mannheim, ProMega, and Life Technologies (Gibco)).

Different techniques can be used depending on the type of liposome desired. For example, small unilamellar vesicles (SUVs) can be prepared by the ultrasonic treatment method, the ethanol injection method, or the French press method, while multilamellar vesicles (MLVs) can be prepared by the reverse-phase evaporation method or by the simple addition of water to a lipid film, followed by dispersal by mechanical agitation (Bangham et al., *J. Mol. Biol.* 13:238-252 (1965)). LUVs can be prepared by the ether injection method, the surfactant method, the Ca$^{2+}$ fusion method, the freeze-thaw method, the reverse-phase evaporation method, the French press method, or the extrusion method.

Average liposome size can be determined by known techniques, such as quasi-elastic light scattering, photon correlation spectroscopy, dynamic light scattering, or various electron microscopy techniques (such as negative staining transmission electron microscopy, freeze fracture electron microscopy or cryo-transmission electron microscopy). In some instances, the resulting liposomes can be run down a Sephadex™ G50 column or similar size exclusion chromatography column equilibrated with an appropriate buffer in order to remove unencapsulated therapeutic agents or detection agents described herein.

Liposomes can range in size, such as from about 50 nm to about 1 µm in diameter. For example, liposomes described herein can be less than about 200 nm in diameter, less than about 160 nm in diameter, or less than about 140 nm in diameter. In some embodiments, liposomes described herein can be substantially uniform in size, for example, 10% to 100%, or more generally at least 10%, 20%, 30%, 40%, 50, 55% or 60%, or at least 65%, 75%, 80%, 85%, 90%, or 95%, or as much as 96%, 97%, 98%, 99%, or 100% of the liposomes can have the same size. In some instances, liposomes can be sized by extrusion through a filter (e.g., a polycarbonate filter) having pores or passages of the desired diameter.

In some instances, liposomes can include a hydrophilic moiety. Attaching a hydrophilic moiety to the surface of liposomes can sterically stabilize liposomes and can increase the circulation longevity of the liposome. This can enhance blood stability and increase circulation time, reduce uptake into healthy tissues, and increase delivery to disease sites such as solid tumors (see, e.g., U.S. Pat. Nos. 5,013,556 and 5,593, 622; and Patel et al., *Crit. Rev. Ther. Drug Carrier Syst.* 9:39 (1992)). The hydrophilic moiety can be conjugated to a lipid component of the liposome, forming a hydrophilic polymer-lipid conjugate. The term "hydrophilic polymer-lipid conjugate", as used herein, refers to a lipid (e.g., a vesicle-forming lipid) covalently joined at its polar head moiety to a hydrophilic polymer, and can be made by attaching the polymer to a reactive functional group at the polar head moiety of the lipid. The covalent linkage can be releasable, such that the polymer dissociates from the lipid (at, e.g., physiological pH or after a variable length of time (see, e.g., Adlakha-Hutcheon et al., *Nat. Biotechnol.* 17:775-779 (1999)). Nonlimiting suitable reactive functional groups include, e.g., amino, hydroxyl, carboxyl, and formyl groups. The lipid can be any lipid described in the art for use in such conjugates. For example, the lipid can be a phospholipid having one or two acyl chains including between about 6 to about 24 carbon atoms in length with varying degrees of unsaturation.

In some circumstances, the lipid in the conjugate can be a phosphatidyethanolamine, such as of the distearoyl form. The polymer can be a biocompatible polymer. In some instances, the polymer has a solubility in water that permits polymer chains to extend away from a liposome surface with sufficient flexibility that produces uniform surface coverage of a liposome. Such a polymer can be a polyalkylether, including PEG, polymethylene glycol, polyhydroxy propylene glycol, polypropylene glycol, polylactic acid, polyglycolic acid, polyacrylic acid and copolymers thereof, as well as those disclosed in U.S. Pat. Nos. 5,013,556 and 5,395,619. The polymer can have an average molecular weight between about 350 daltons and about 10,000 daltons.

Micelles

The present disclosure includes siRNA molecules reversibly conjugated to a phospholipid of a micelle. One exemplary micelle is depicted in FIG. 2A. Upon exposure to reducing conditions, such as within a cell, the siRNA is unconjugated from the phospholipid of the micelle and can inhibit expression of a target polypeptide. Micelles are vesicles that include a single lipid monolayer encapsulating an aqueous phase. Micelles can be spherical or tubular and form spontaneously about the critical micelle concentration ("CMC"). In general, micelles are in equilibrium with the monomers under a given set of physical conditions such as temperature, ionic environment, concentration, etc.

Micelles are formed in the presence of "micelle-forming compounds", which include amphipathic lipids (e.g., a vesicle-forming lipid as described herein or known in the art), lipoproteins, detergents, non-lipid polymers, or any other compound capable of either forming or being incorporated into a monolayer vesicle structure. Thus, a micelle-forming compound includes compounds that are capable of forming a monolayer by themselves or when in combination with another compound, and may be polymer micelles, block co-polymer micelles, polymer-lipid mixed micelles, or lipid micelles. A micelle-forming compound, in an aqueous environment, generally has a hydrophobic moiety in contact with the interior of the vesicle, and a polar head moiety oriented outwards into the aqueous environment. Hydrophilicity generally arises from the presence of functional groups, such as hydroxyl, phosphate, carboxyl, sulfate, amino or sulfhydryl groups. Hydrophobicity generally results from the presence of a long chain of aliphatic hydrocarbon groups.

A micelle can be prepared, e.g., from lipoproteins or artificial lipoproteins including low density lipoproteins, chylomicrons and high density lipoproteins. Micelles can be generated using a variety of known techniques, including, without limitation, simple dispersion by mixing in aqueous or hydroalcoholic media or media containing surfactants or ionic substances; sonication; solvent dispersion; or any other technique described herein or known in the art. Different techniques can be used, depending on the type of micelle desired and the physicochemical properties of the micelle-forming components, such as solubility, hydrophobicity and behavior in ionic or surfactant-containing solutions.

Micelles can range in size, such as between about 5 nm to about 50 nm in diameter. In some instances, micelles can be less than about 50 nm in diameter, less than about 30 nm in diameter, or less than about 20 nm in diameter.

In some situations, micelles described herein can include a hydrophilic polymer-lipid conjugate, as described herein or known in the art.

Conjugation

The siRNA can be specifically modified such that it can be conjugated to that phospholipid. For example, one or more nucleotides of an siRNA can be modified to include a carboxylic acid functionality, and a phospholipid can be modified with an amine. The amine would then be capable of reacting with the carboxylic acid functionality on the siRNA, using procedures known in the art, to form an amide linkage between the phospholipid and siRNA. Alternatively, the siRNA can be modified with an amine and reacted with a carboxylic functionality on a phospholipid to form an amide linkage. Nonlimiting examples of other functionalities that react with amines are acyl chlorides, acid anhydrides, esters, and carboxylic salts.

The siRNA-phospholipid conjugate can be linked, for example, via amide linkages. One particular mechanism of producing carbamide linkages includes the use of alkyl chloroformate groups. In one such nonlimiting example, a phospholipid with a chloroformate group is reacted with an siRNA having an amine group functionality in the presence of a base. The resulting compound is a siRNA-phospholipid conjugated by a carbamide linkage.

An siRNA can also be conjugated to a phospholipid via an ester bond. A common method of performing such esterifications is the use of Steglich esterification. In this example, siRNAs are modified with carboxylic acid functionalities at one or more positions. The carboxylic acids are then activated with dicyclohexylcarbodiimide. Subsequently, 4-dimethylaminopyridine is used to catalyze an acyl-transfer with a hydroxyl group on the phospholipid.

In addition, siRNAs can be conjugated to a phospholipid via an ether linkage. Such a linkage can be made using procedures known in the art, such as Williamson ether synthesis reaction. The Williamson reaction involves using sodium hydroxide or another base to form an alkoxide of an alcohol on the siRNA. The phospholipid to be linked can be an aliphatic compound bearing a suitable leaving group, such as an iodide, bromide, or sulfonate leaving group.

Another useful conjugate is an siRNA disulfide linked to a phospholipid, such as an siRNA-S-S-PE (e.g., 1,2-Dipalmitoyl-sn-Glycero-3-Phosphothioethanol). By activating the 3'-sense strand of a hexylamine-modified-siRNA with the pyridyldisulfide containing crosslinker N-succinimidyl-3-(2-pyridyldithio)propionate (SPDP), the activated siRNA-PDP reacts with the —SH group of the phosphothiethanol (PE-SH) forming a reversible disulfide bond (according to FIG. 2). Another useful pyridyl disulfide-containing crosslinker is 4 saccinimidyloxycarbonyl-x-methyl-x-(2-pyridyldithio) toluene (SMPT).

One distinguishing characteristic of this conjugate is the chemical binding between the siRNA and a phospholipid (PE-SH), instead of classical binding based on electrostatic interactions between negative and positive charges respectively. The chemical conjugation improves the siRNA stability against nucleases attack, but also provides a reversible bond able to be hydrolyzed into the natural cytosolic environment, freeing the siRNA to act into the cells. The technique can be applied to any kind of siRNA which mediates the knock-down of different genes.

Detection Agents

In some instances, the liposomes or micelles described herein, e.g., a liposome or micelle reversibly conjugated to an siRNA, can be used to detect or image cells, e.g., using a liposome or micelle that includes a detection agent. The detection agent can be used to qualitatively or quantitatively analyze the location and/or the amount of a liposome or micelle at a particular locus. The detection agent can also be used to image a liposome, micelle, and/or a cell or tissue target of a liposome or micelle using standard methods.

A liposome or micelle described herein can be derivatized (or labeled) with a detection agent by attaching the agent to a component or a phospholipid of the liposome or micelle. Nonlimiting examples of detection agents include, without limitation, fluorescent compounds, various enzymes, prosthetic groups, luminescent materials, bioluminescent materials, fluorescent emitting metal atoms, (e.g., europium (Eu)), radioactive isotopes (described below), quantum dots, electron-dense reagents, and haptens. The detection reagent can be detected using various means including, but are not limited to, spectroscopic, photochemical, radiochemical, biochemical, immunochemical, or chemical means.

Nonlimiting exemplary fluorescent detection agents include fluorescein, fluorescein isothiocyanate, rhodamine, 5-dimethylamine-1-naphthalenesulfonyl chloride, phycoerythrin, and the like. A detection agent can also be a detectable enzyme, such as alkaline phosphatase, horseradish peroxidase, β-galactosidase, acetylcholinesterase, glucose oxidase and the like. When a liposome or micelle is derivatized with a detectable enzyme, it can be detected by adding additional reagents that the enzyme uses to produce a detectable reaction product. For example, when the detection agent is horseradish peroxidase, the addition of hydrogen peroxide and diaminobenzidine leads to a detectable colored reaction product. A liposome or micelle can also be derivatized with a prosthetic group (e.g., streptavidin/biotin and avidin/biotin). For example, a liposome or micelle can be derivatized with biotin and detected through indirect measurement of avidin or streptavidin binding. Nonlimiting examples of fluorescent compounds that can be used as detection reagents include umbelliferone, fluorescein, fluorescein isothiocyanate, rhodamine, dichlorotriazinylamine fluorescein, dansyl chloride, and phycoerythrin. Luminescent materials include, e.g., luminol, and bioluminescent materials include, e.g., luciferase, luciferin, and aequorin.

A detection agent can also be a radioactive isotope, such as, but not limited to, α-, β-, or γ-emitters; or β- and γ-emitters. Radioactive isotopes can be used in diagnostic or therapeutic applications. Such radioactive isotopes include, but are not limited to, iodine ($^{131}$I or $^{125}$I), yttrium ($^{90}$Y), lutetium ($^{177}$Lu), actinium ($^{225}$Ac), praseodymium ($^{142}$PR or $^{143}$Pr), astatine ($^{211}$At), rhenium ($^{186}$Re or $^{187}$Re), bismuth ($^{212}$Bi or $^{213}$Bi), indium ($^{111}$In), technetium ($^{99m}$Tc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), and gallium ($^{67}$Ga).

The liposomes or micelles can be radiolabeled using techniques known in the art. In some situations, a liposome or micelle described herein is contacted with a chelating agent, e.g., 1,4,7,10-tetraazacyclododecane-N,N',N",N"'-tetraacetic acid (DOTA), to thereby produce a conjugated liposome or micelle. The conjugated liposome or micelle is then radiolabeled with a radioisotope, e.g., $^{111}$In, $^{90}$Y, $^{177}$Lu, $^{186}$Re, $^{187}$Re, or $^{99m}$Tc, to thereby produce a labeled liposome or micelle. In other methods, the liposome or micelle can be labeled with $^{111}$In and $^{90}$Y using weak transchelators such as citrate (see, e.g., Khaw et al., *Science* 209:295-297 (1980)) or $^{99m}$Tc after reduction in reducing agents such as Na Dithionite (see, e.g., Khaw et al., *J. Nucl. Med.* 23:1011-1019 (1982)) or by SnCl$_2$ reduction (see, e.g., Khaw et al., *J. Nucl. Med.* 47:868-876 (2006)). Other methods are described in, e.g., Lindegren et al., *Bioconjug. Chem.* 13:502-509 (2002); Boyd et al., *Mol. Pharm.* 3:614-627 (2006); and del Rosario et al., *J. Nucl. Med.* 34:1147-1151 (1993).

Targeting Agents

The conjugated siRNA composition can include a targeting agent, e.g., attached to a phospholipid of the liposome or micelle of the composition, or to an siRNA and/or PEG of the composition. The targeting agents can be, for example, various specific ligands, such as antibodies, monoclonal antibodies and their fragments, folate, mannose, galactose and other mono-, di-, and oligosaccharides, and RGD peptide.

The liposomes and micelles of the compositions described herein are not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to receptors. In some instances, a liposome or micelle described herein can be conjugated to one, two, or more of a variety of targeting agents. For example, when two or more targeting agents are used, the targeting agents can be similar or dissimilar. Utilization of more than one targeting agent on a particular liposome or micelle can allow the targeting of multiple biological targets or can increase the affinity for a particular target.

The targeting agents can be associated with the liposomes or micelles reversibly conjugated to an siRNA in a number of ways. For example, the targeting agents can be associated (e.g., covalently or noncovalently bound) to a phospholipid of the liposome or micelle with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages.

In addition, a liposome or micelle reversibly conjugated to an siRNA can also incorporate reactive groups (e.g., amine groups such as polylysine, dextranemine, profamine sulfate, and/or chitosan). The reactive group can allow for further attachment of various specific ligands or reporter groups (e.g., $^{125}$I, $^{131}$I, I, Br, various chelating groups such as DTPA, which can be loaded with reporter heavy metals such as $^{111}$In, $^{99m}$Tc, Gd, Mn, fluorescent groups such as FITC, rhodamine, Alexa, and quantum dots), and/or other moieties (e.g., ligands, antibodies, and/or portions thereof).

Antibodies as Targeting Agents

In some instances, the targeting agents for a liposome or micelle reversibly conjugated to an siRNA are antigen binding proteins or antibodies or binding portions thereof. Antibodies can be generated to allow for the specific targeting of antigens or immunogens (e.g., tumor, tissue, or pathogen specific antigens) on various biological targets (e.g., pathogens, tumor cells, normal tissue). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')$_2$); or biosynthetic antibodies, e.g., single chain antibodies, single domain antibodies (DAB), Fvs, or single chain Fvs (scFv).

In certain instances, the targeting agent is an antibody the specifically binds an angiogenesis agent described herein. For example, the targeting agent is an anti-VEGF antibody described herein, e.g., bevacizumab. In other examples, the liposome or micelle includes, in addition to an anti-angiogenesis agent described herein, an additional antibody that targets additional ligands.

Methods of making and using polyclonal and monoclonal antibodies are well known in the art, e.g., in Harlow et al., *Using Antibodies: A Laboratory Manual: Portable Protocol I*. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, *Monoclonal Antibodies: Preparation and Use of Monoclonal Antibodies and Engineered Antibody Derivatives*, Springer Verlag (Dec. 15, 2000; 1st edition).

Antibody attachment can be performed via any method that does not compromise the ability of the antibody to target a tumor, and to treat it, e.g., by binding to a specific antiangiogenesis factor. For example, attachment can be performed through standard covalent binding to free amine groups (see, e.g., Torchilin et al., *Hybridoma* 6:229-240 (1987); Torchilin et al, *Biochim. Biophys. Acta* 1511:397-411 (2001); Masuko et al., *Biomacromol.* 6:800-884 (2005)).

Signal Peptides as Targeting Agents

In some instances, a targeting agent for a liposome or micelle reversibly conjugated to an siRNA can be a signal peptide. These peptides can be chemically synthesized or cloned, expressed and purified using known techniques. Signal peptides can be used to target the liposomes or micelles described herein to a target cell or tissue.

Nucleic Acids as Targeting Agents

In other instances, the targeting agent for a liposome or micelle reversibly conjugated to an siRNA is a nucleic acid (e.g., RNA or DNA). In some examples, the nucleic acid targeting agents are designed to hybridize by base pairing to a particular nucleic acid (e.g., chromosomal DNA, mRNA, or ribosomal RNA). In other situations, the nucleic acids bind a ligand or biological target. For example, the nucleic acid can bind reverse transcriptase, Rev or Tat proteins of HIV (Tuerk et al., *Gene* 137:33-9 (1993)); human nerve growth factor (Binkley et al., *Nuc. Acids Res.* 23:3198-205 (1995)); or vascular endothelial growth factor (Jellinek et al., *Biochem.* 83:10450-10456 (1994)). Nucleic acids that bind ligands can be identified by known methods, such as the SELEX procedure (see, e.g., U.S. Pat. Nos. 5,475,096; 5,270,163; and 5,475,096; and WO 97/38134; WO 98/33941; and WO 99/07724). The targeting agents can also be aptamers that bind to particular sequences.

Other Targeting Agents

The targeting agents for a liposome or micelle reversibly conjugated to an siRNA can recognize a variety of epitopes on preselected biological targets (e.g., pathogens, tumor cells, or normal cells). For example, in some instances, the targeting agent can be sialic acid to target HIV (Wies et al., *Nature* 333:426 (1988)), influenza (White et al., *Cell* 56:725 (1989)), *Chlamydia* (*Infect. Immunol.* 57:2378 (1989)), *Neisseria meningitidis, Streptococcus suis, Salmonella*, mumps, newcastle, reovirus, Sendai virus, and myxovirus; and 9-OAC sialic acid to target coronavirus, encephalomyelitis virus, and rotavirus; non-sialic acid glycoproteins to target cytomegalovirus (*Virol.* 176:337 (1990)) and measles virus (*Virol.* 172: 386 (1989)); CD4 (Khatzman et al., *Nature* 312:763 (1985)), vasoactive intestinal peptide (Sacerdote et al., *J. Neurosci. Res.* 18:102 (1987)), and peptide T (Ruff et al., *FEBS Letters* 211:17 (1987)) to target HIV; epidermal growth factor to target vaccinia (Epstein et al., *Nature* 318:663 (1985)); acetylcholine receptor to target rabies (Lentz et al., *Science* 215: 182 (1982)); Cd3 complement receptor to target Epstein-Barr virus (Carel et al., *J. Biol. Chem.* 265:12293 (1990)); beta-adrenergic receptor to target reovirus (Co et al., *Proc. Natl. Acad. Sci. USA* 82:1494 (1985)); ICAM-1 (Marlin et al., *Nature* 344:70 (1990)), N-CAM, and myelin-associated glycoprotein MAb (Shephey et al., *Proc. Natl. Acad. Sci. USA* 85:7743 (1988)) to target rhinovirus; polio virus receptor to target polio virus (Mendelsohn et al., *Cell* 56:855 (1989)); fibroblast growth factor receptor to target herpes virus (Kaner et al., *Science* 248:1410 (1990)); oligomannose to target *Escherichia coli*; and ganglioside $G_{M1}$ to target *Neisseria meningitides*.

In other instances, the targeting agent targets liposomes or micelles reversibly conjugated to an siRNA to factors expressed by oncogenes. These can include, but are not limited to, tyrosine kinases (membrane-associated and cytoplasmic forms), such as members of the Src family; serine/threonine kinases, such as Mos; growth factor and receptors, such as platelet derived growth factor (PDDG), small GTPases (G proteins), including the ras family, cyclin-dependent protein kinases (cdk), members of the myc family members, including c-myc, N-myc, and L-myc, and bcl-2 family members.

In addition, vitamins (both fat soluble and non-fat soluble vitamins) can be used as targeting agents to target biological targets (e.g., cells) that have receptors for, or otherwise take up, vitamins. For example, fat soluble vitamins (such as vitamin D and its analogs, vitamin E, vitamin A), and water soluble vitamins (such as vitamin C) can be used as targeting agents.

Polyethylene Glycol

In some instances, phospholipids of a micelle or liposome described herein can be modified with or conjugated to polyethylene glycol (PEG). Nonlimiting examples of PEG that can be used in the methods and compositions described herein include PEGs having a molecular weight of about 200 to about 20,000 daltons.

To couple PEG to a phospholipid, the PEG can be activated by preparing a derivative of the PEG having a reactive group at one terminus. Many activated derivatives of PEG are known in the art. One nonlimiting example of an activated PEG derivative is the succinimidyl succinate ester of PEG (see, e.g., U.S. Pat. No. 4,179,337). Other nonlimiting examples of activated PEG molecules that can be used in the methods described herein include PEGs having a reactive cyanuric chloride moiety, succinimidyl carbonates of PEG, phenylcarbonates of PEG, imidazolyl formate derivatives of PEG, PEG-carboxymethyl azide, PEG-imidoesters, PEG-vinyl sulfone, active ethyl sulfone derivatives of PEG, tresylates of PEG, PEG-phenylglyoxal, PEGs activated with an aldehyde group, PEG-maleimides, and PEGs with a terminal amino moiety. These PEG derivatives and methods for conjugating such derivatives to agents are known in the art (see, e.g., Zalipsky et al., "Use of Functionalized Poly(Ethylene Glycol)s for Modification of Polypeptides", in *Use of Polyethylene Glycol Chemistry. Biotechnical and Biomedical Applications*, J. M. Harris, Ed., Plenum Press, New York (1992); see also Zalipsky, *Adv. Drug Rev.* 16:157-182 (1995)).

Therapeutic Administration

The route and/or mode of administration of a liposome or micelle reversibly conjugated to an siRNA, described herein, can vary depending upon the desired results. One with skill in the art, i.e., a physician, is aware that dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner.

In some instances, a liposome or micelle reversibly conjugated to an siRNA, described herein (e.g., a pharmaceutical formulation of a liposome or a micelle) can effectively cross the blood brain barrier and enter the brain. In other instances, a liposome or micelle can be delivered using techniques designed to permit or to enhance the ability of the formulation to cross the blood-brain barrier. Such techniques are known in the art (e.g., WO 89/10134; Cloughesy et al., *J. Neurooncol.* 26:125-132 (1995); and Begley, *J. Pharm. Pharmacol.* 48:136-146 (1996)). Components of a formulation can also be modified (e.g., chemically) using methods known in the art to facilitate their entry into the CNS.

For example, in some instances, a liposome or micelle reversibly conjugated to an siRNA, described herein, is administered locally. This is achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, a liposome or micelle described herein is introduced into the central nervous system, circulatory system or gastrointestinal tract by any suitable route, including intraventricular, intrathecal injection, paraspinal injection, epidural injection, enema, and by injection adjacent to a peripheral nerve.

Pulmonary administration can also be employed, e.g., by use of an inhaler or nebulizer, and formulation with an aerosolizing agent, or via perfusion in a fluorocarbon or synthetic pulmonary surfactant.

A liposome or micelle reversibly conjugated to an siRNA, described herein, can be formulated as a pharmaceutical composition that includes a suitable amount of a physiologically acceptable excipient (see, e.g., *Remington's Pharmaceutical Sciences* pp. 1447-1676 (Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Water is a particularly useful excipient when a liposome or micelle described herein is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in *Remington's Pharmaceutical Sciences* (ibid.). The pharmaceutical compositions, if desired, can also contain minor amounts of wetting or emulsifying agents, or pH buffering agents.

Liquid carriers can be used in preparing solutions, suspensions, emulsions, syrups, and elixirs containing a liposome or micelle reversibly conjugated to an siRNA, described herein. A liposome or micelle reversibly conjugated to an siRNA, described herein, can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, a liposome or micelle reversibly conjugated to an siRNA, described herein, is formulated for intravenous administration. Compositions for intravenous administration can comprise a sterile isotonic aqueous buffer. The compositions can also include a solubilizing agent. Compositions for intravenous administration can optionally include a local anesthetic such as lignocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where a liposome or micelle described herein is administered by infusion, it can be dispensed, for example, with an infusion bottle containing sterile pharmaceutical grade water or saline. Where a liposome or micelle described herein is administered by injection, an ampule of sterile water for injection or saline can be provided so that the ingredients can be mixed prior to administration.

A liposome or micelle reversibly conjugated to an siRNA, described herein, can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of a liposome or micelle described herein that is effective for inhibiting the expression of a target polypeptide, and/or treating a disorder or disease, can be determined using standard laboratory and clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. For example, the dose of a liposome or micelle described herein can each range from about 0.001 mg/kg to about 250 mg/kg of body weight per day, from about 1 mg/kg to about 250 mg/kg body weight per day, from about 1 mg/kg to about 50 mg/kg body weight per day, or from about 1 mg/kg to about 20 mg/kg of body weight per day. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner.

In some instances, a pharmaceutical composition containing a liposome or micelle reversibly conjugated to an siRNA, described herein, is in unit dosage form, e.g., as a tablet, capsule, powder, solution, suspension, emulsion, granule, or suppository. In such form, the pharmaceutical composition can be sub-divided into unit doses containing appropriate quantities of a liposome or micelle described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Kits

A liposome or micelle reversibly conjugated to an siRNA, described herein, can be provided in a kit. In some instances, the kit includes (a) a container that contains a liposome or micelle reversibly conjugated to an siRNA, described herein, and, optionally (b) informational material. The informational material can be descriptive, instructional, marketing or other material that relates to the methods described herein and/or the use of the liposome or micelle, e.g., for therapeutic benefit.

The informational material of the kits is not limited in its form. In some instances, the informational material can include information about production of the liposome or micelle, molecular weight of the liposome or micelle, concentration, date of expiration, batch or production site information, and so forth. In other situations, the informational material relates to methods of administering the liposome or micelle, e.g., in a suitable amount, manner, or mode of administration (e.g., a dose, dosage form, or mode of administration described herein). The method can be a method of treating a subject having a disorder.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about the liposomes or micelles therein and/or their use in the methods described herein. The informational material can also be provided in any combination of formats.

In addition to the liposome or micelle, the kit can include other ingredients, such as a solvent or buffer, a stabilizer, or a preservative. The kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

The kit can include one or more containers for the liposomes or micelles or other agents. In some cases, the kit contains separate containers, dividers or compartments for the liposomes or micelles and informational material. For example, the liposomes or micelles can be contained in a bottle, vial, or syringe, and the informational material can be contained in a plastic sleeve or packet. In other situations, the separate elements of the kit are contained within a single, undivided container. For example, the liposomes or micelles can be contained in a bottle, vial or syringe that has attached thereto the informational material in the form of a label. In some cases, the kit can include a plurality (e.g., a pack) of individual containers, each containing one or more unit dosage forms (e.g., a dosage form described herein) of the liposomes or micelles. The containers can include a unit dosage, e.g., a unit that includes the liposomes or micelles. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of the liposomes or micelles, e.g., a syringe or other suitable delivery device. The device can be provided pre-loaded with liposomes or micelles, e.g., in a unit dose, or can be empty, but suitable for loading.

EXAMPLES

Those skilled in the art will recognize, or be able to ascertain, using no more than routine experimentation, numerous equivalents to the specific substances and procedures described herein. Such equivalents are intended to be encompassed in the scope of the claims that follow the examples below.

I. Methods

A. Materials

The GFP-siRNA modified with an SPDP group (N-Succinimidyl 3-(2-pyridyldithio)-propionate) at the 3'-end of its sense strand [sense strand: (from 5' to 3') AGCUGAC-CCUGAAGUUCAUTT-SPDP], and the L-glutathione (reduced) were obtained from Invitrogen (Carlsbad, Calif.) and Sigma-Aldrich (St. Louis, Mo.), respectively. The 1,2-di-palmitoyl-sn-glycero-3-phosphothioethanol (PE-SH, MW 731) and 1,2-distearoyl-sn-glycero-3-phosphoethanolamine-N-[methoxy(polyethylene glycol)-2000] (PEG-PE) were obtained from Avanti Polar Lipids (Alabaster, Ala.). The d-Salt™ dextran desalting column was obtained from Pierce (Rockford, Ill.). Triethylammonium acetate (TEAA) 1M and chloroform ($CH_3Cl$) were obtained from Sigma-Aldrich (St. Louis, Mo.) and Fisher Scientific (Fair Lawn, N.J.), respectively. The RNase/DNase free water was obtained from MP Biomedicals (Solon, Ohio) and the phosphate saline buffer (PBS) 10× solution was obtained from Fisher Scientific (Fair Lawn, N.J.). RNase III $E.\ coli$ was obtained from Ambion (Austin, Tex.). The thin layer chromatography (TLC) was obtained from EMD Chemicals Inc. (Gibbstown, N.J.). Pre-cast 20% TBE gels, SYBR® Gold Nucleic Acid Gel Stain, and Lipofectamine™ 2000 Reagent were obtained from Invitrogen.

B. Cell Culture

GFP-expressing C166 endothelial cells were grown in DMEM, at 37° C. and 5% $CO_2$. DMEM and supplements (fetal bovine serum, penicillin, streptomycin and amphotericin B), Trypan Blue Solution and Trypsin were obtained from CellGro (Kansas City, Mo.).

C. Synthesis of siRNA-S-S-PE Conjugate

A solution of the SPDP-activated siRNA (20 nmoles) in PBS, pH 7.4 (120 µl) was added dropwise to a solution of PE-SH (2 µmoles) in DMSO and $CHCl_3$ (total volume of organic solvents 350 µl). The reaction was carried out for 48 h at RT with continuous shaking. The unreacted PE-SH was removed on a desalting column. The collected samples containing the siRNA-conjugate were ultracentrifuged for 1 min at 14.5×1000 rpm to further remove mixed solvents and/or PE-SH. The siRNA-S-S-PE conjugate was stored at −20° C.

D. Cleavage of Disulfide Bond by TLC

To verify that the disulfide bond in siRNA-S-S-PE conjugate was cleavable in reductive conditions, siRNA-S-S-PE (0.5-1 µg) was incubated with 25 µL of a GSH solution (10 mM) in PBS, pH 7.4 (the concentration of GSH in the cytosol can reach 10 mM). A known amount of the conjugate was lyophilized and then incubated with the GSH solution at 37° C. for 4 h with continuous shaking. The sample was immediately frozen at −80° C., then lyophilized and finally redissolved in water for analysis by TLC using a mobile phase of $CHCl_3$:MeOH/8:2. After the TCL was dried, it was dipped in Molybdenum Blue dye to highlight the presence of a blue spot corresponding to liberated phospholipid.

E. Preparation of siRNA-S-S-PE/PEG-PE Nanosized Mixed Micelles

A thin polymeric film of PEG-PE was prepared from a chloroform solution (as described in Musacchio et al., *Mol. Pharm.* 6:468-479 (2009) and Sawant et al., *Int. J. Pharm.* 374:114-118 (2009)). Chloroform was removed by $N_2$, and the film was further dried under vacuum. A siRNA-conjugate in water was added to the PEG-PE film at weight ratios of 1:200, 1:500, and 1:750 in a final total volume of 300 µl, and the system was extensively vortexed to form nanosized mixed micelles.

F. Micelle Properties

Micelle mean size and size distribution were determined by dynamic light scattering (DLS) using a Zeta Plus Instrument (Brookhaven Instrument Co., Holtsville, N.Y.). Size distribution and morphology of siRNA-containing mixed micelles were also examined using a transmission electron microscopy (TEM). Various samples of PEG-PE and siRNA-S-S-PE/PEG-PE micelles were diluted to a concentration of 1 mg/mL in deionized water. The micelles were stained with 1% uranyl acetate (as described in Tang et al., *J. Natl. Cancer Inst.* 99:1004-1015 (2007)), placed on a circular copper grid and examined with a JEOL JEM-1010 electron microscope (JEOL USA, Inc, Peabody, Mass.).

Zeta-potential (ζ) of all micelle formulations (diluted in 1 mM KCl) was measured by a Zeta Phase Analysis Light Scattering (PALS) with an ultrasensitive zeta potential analyzer instrument (Brookhaven Instruments, Holtsville, N.Y.).

G. siRNA-S-S-PE Conjugate Incorporation into PEG-PE Nanosystem by HPLC

All micelle formulations were analyzed by HPLC (Hitachi, L-7450A) equipped with a UV detector at 260 nm on a XBridge C18 column (Waters, Milford, Mass.). The analyses were carried out at RT with a mobile phase A composed of 5% acetonitrile in 0.1 M TEAA, pH 7, and mobile phase B of 15% of acetonitrile in 0.1 M TEAA. The analyses were run in a gradient elution from 20% to 58% of B in 15 min with a 1 min/ml flow rate. The same concentration (1.5 µg/50 µl) of freshly synthesized siRNA-S-S-PE conjugate alone and formulated as different weight ratios of mixed micelles were compared, and the degree of incorporation was evaluated by normalizing the area under the peak of free siRNA-conjugate and the siRNA-conjugate in mixed micelles at the same retention time ($t_r$ about 12 mins). As a reference, plain PEG-PE micelles were used.

H. Stability of siRNA Against Degradation by RNase

Freshly prepared siRNA-S-S-PE conjugate was formulated with PEG-PE into a 1:750 (wt/wt) mixed micelle preparation (a total amount of 4.8 µg siRNA-S-S-PE) in a final volume of 100 µl. RNAse III *E. coli* was added to the formulation and the sample was incubated at 37° C. The stability of siRNA in mixed micelles was compared to that of the native siRNA over a 24 h period. At determined time-points, an aliquot of the sample was withdrawn, frozen in dry ice to stop the progression of degradation and stored at −80° C. until the moment of the analysis. Nucleic acid degradation was visualized by gel electrophoresis (20% TBE gel). The analysis was carried out according to the conditions suggested by the provider. The bands were stained with SYBR® Gold Nucleic Acid Gel Stain in TBE buffer, and visualized by Kodak MI software.

I. GFP Down-Regulation in C166-GFP Endothelial Cells Estimated by Flow
Cytometry GFP-C166 endothelial cells were grown in 25 cm² flasks at 37° C. and 5% $CO_2$ in DMEM containing 10% FBS until 80% confluent. $3.5 \times 10^4$ cells/well were seeded in twelve-well plates. After an overnight incubation (confluence about 80%), they were washed once using DMEM (1 mL) and incubated with siRNA-S-S-PE/PEG-PE micelle formulations (each containing 84 nM siRNA). For comparisons, the same concentration of naked siRNA and siRNA in Lipofectamine were used. Fresh micelle samples were incubated in 300 µl of DMEM with 10% FBS. After 4 h incubation, the medium was replaced with 1 ml of fresh DMEM, and kept for a total of 48 h. Untreated cells were used as a control. After the incubation, the cells were washed once with 200 µl of trypsin solution to remove inactivating traces of serum, detached with an additional 200 µl, collected in 15 ml test tubes, and fixed in 1 ml of a 4% paraformaldehyde solution (at 4° C.) until analysis by flow cytometry (BD FACSCalibur). The gene silencing percentage was expressed as the average of three independent experiments.

J. Cytotoxicity by Trypan Blue Exclusion

The cell viability after the incubation with siRNA micelle formulations, naked siRNA and siRNA in Lipofectamine was tested in the same conditions used for the GFP-gene silencing test by the Trypan Blue solution exclusion assay. After incubation with micelles, the cells were washed once with DMEM and once more with 200 µl of trypsin solution. When the cells were detached from the bottom of the well, a 5-fold volume excess of complete DMEM was added. The cells were recovered and counted in Trypan Blue solution on a known dilution of cell suspension. Cell viability of each formulation was expressed as a percentage of the total number of the treated cells versus the total number of the untreated cells. The experiment was done in triplicate on three different sample preparations.

II. Results

A. siRNA-S-S-PE Conjugate

The PE-SH was conjugated to the 3'-end of the modified siRNA sense strand by introducing a disulfide linkage according the schematic in FIG. 1A. The formation of the siRNA-S-S-PE conjugate was confirmed by its cleavability in a 10 mM GSH solution, mimicking intracellular reductive conditions. Equal amounts of siRNA-S-S-PE conjugate before (C) and after hydrolysis (H), and free PE (P) were run on TLC (FIG. 1B). Two spots were revealed for the sample H, corresponding to the liberated siRNA (lower spot) and cleaved phospholipid (upper spot). The starting siRNA-conjugate showed no impurities before the incubation in the GHS solution. The free PE-SH and the cleaved phospholipid had different retention factors compared to each other due to the different dissolving media used (chloroform for the free PE-SH and buffer for the cleaved one) that can affect the run on the TLC.

B. Nanosized Mixed Micelles of siRNA-S-S-PE and PEG-PE

The siRNA-S-S-PE conjugate incorporated readily into PEG-PE micelles via the PE moiety. The schematic structure of the resulting mixed micelle is shown in FIG. 2A. Both plain PEG-PE micelles and siRNA-S-S-PE/PEG-PE mixed micelles had a mean size around 10 nm by dynamic light scattering (FIG. 2B). Transmission electron microscopy (TEM) analysis demonstrated the round shape and confirmed their narrow size distribution (FIG. 2C). FIGS. 2B and 2C present the size distribution data for the 1:750 (wt/wt) siRNA-S-S-PE/PEG-PE micelles (similar results were obtained for 1:200 and 1:500 mixed micelles).

Zeta potential ($\zeta$) measurements of the mixed micelle and plain PEG-PE micelle suspensions diluted with 1 mM KCl demonstrated that the surface charge of siRNA-containing micelles was more negative ($\zeta=-28.3\pm5.6$ mV) than that of the plain PEG-PE micelles ($\zeta=-13.2\pm3.2$ mV) (FIG. 2D).

Figures 3A, 3B, 3C, 3D, 3E:
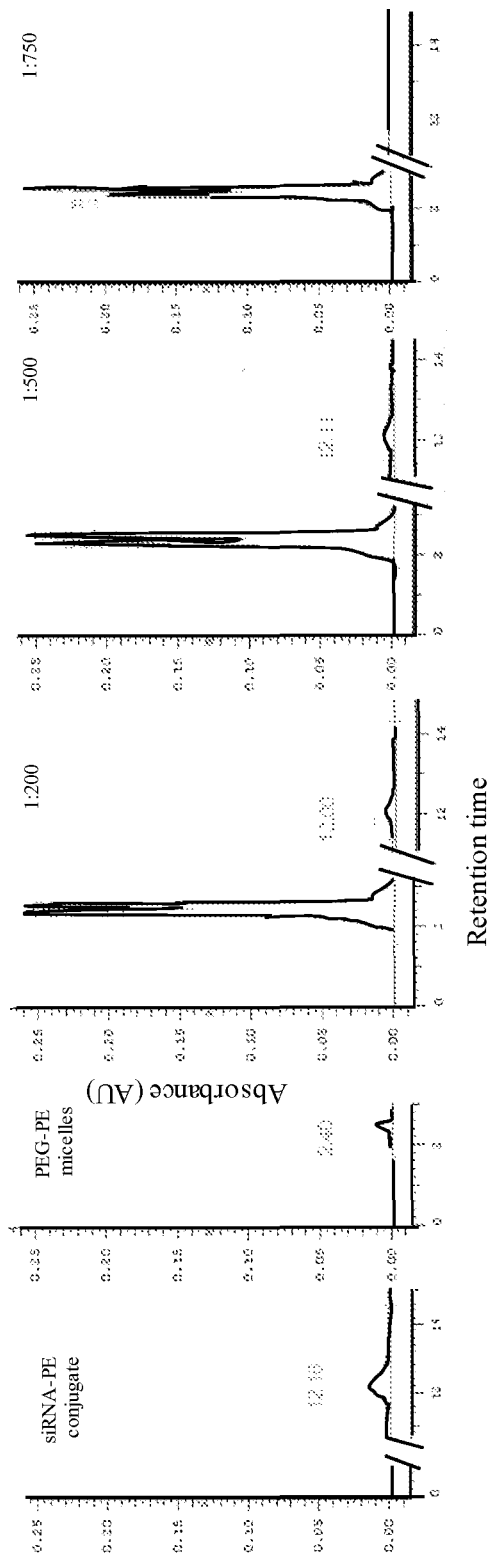
FIG. 3 is a series of graphic representations of HPLC absorbance versus retention times for siRNA-S-S-PE conjugate micelles (FIG. 3A), PEG-PE micelles (FIG. 3B), and siRNA-S-S-PE conjugate micelles at 1:200 (wt/wt) (FIG. 3C), 1:500 (wt/wt) (FIG. 3D), and 1:750 (wt/wt) (FIG. 3E).

HPLC analysis demonstrated that the peak at about 2.5 min corresponded to siRNA-S-S-PE-containing mixed micelles, while the peak at about 12 min corresponded to the free siRNA conjugate (FIG. 3A). Plain PEG-PE micelles injected at the same concentration as mixed micelles showed a small peak at 2.5 min at 260 nm (FIG. 3B). The increase of the area at this $t_r$ for mixed micelles was attributed to the presence of the siRNA-S-S-PE conjugate in the PEG-PE micelles. Chromatography also confirmed that in the formulations with weight ratios of 1:200 and 1:500, siRNA had 62 and 69% incorporation respectively (FIGS. 3C and 3D), while at the 1:750 ratio (FIG. 3E) quantitative incorporation of siRNA conjugate into the mixed micelles was observed (no free siRNA conjugate peak was seen at 12 min).

C. Stability Against Digestion by RNase

Figures 4A, 4B:
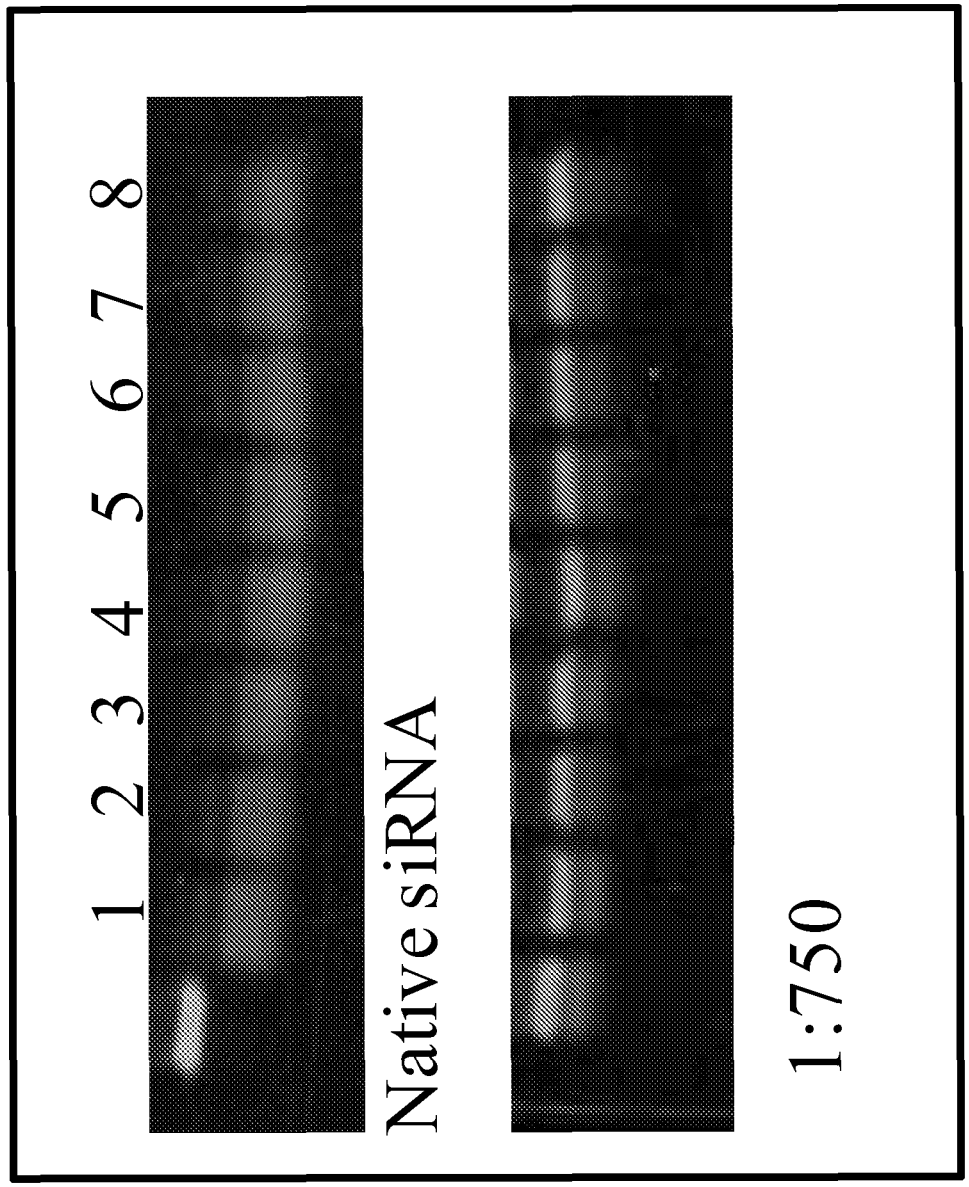
FIG. 4 is a representation of a gel electrophoresis of native (unmodified) siRNA (FIG. 4A) and siRNA-S-S-PE/PEG-PE mixed micelles (1:750 wt/wt) (FIG. 4B) either before or after incubation with RNAse.

To test the stability of siRNA wrapped into PEG-PE nanoparticles against enzymatic degradation, siRNA-S-S-PE/PEG-PE mixed micelles were prepared at a 1:750 weight ratio and incubated in the presence of RNase III from *E. coli* for 24 h at 37° C. The degradation of siRNA was studied by gel electrophoresis by following the fluorescence intensity of the siRNA after SYBR gold gel staining. As shown in FIG. 4B, there were no degradation products of siRNA in PEG-PE micelles after over 24 h (the same amount of siRNA not exposed to RNase was used as a positive control). In FIG. 4, the first lane represents the siRNA not digested and used as reference for both naked siRNA and siRNA-S-S-PE in mixed micelles; 1=30 mins incubation in RNAse solution, 2=1 h, 3=2 h, 4=3 h, 5=4 h, 6=5 h, 7=6 h, and 8=24 h incubation, respectively. The enzymatic degradation of free (native) siRNA was evident after 30 min (FIG. 4A).

D. GFP-Silencing in GFP-C166 Endothelial Cells

Figures 5A, 5B, 5C:
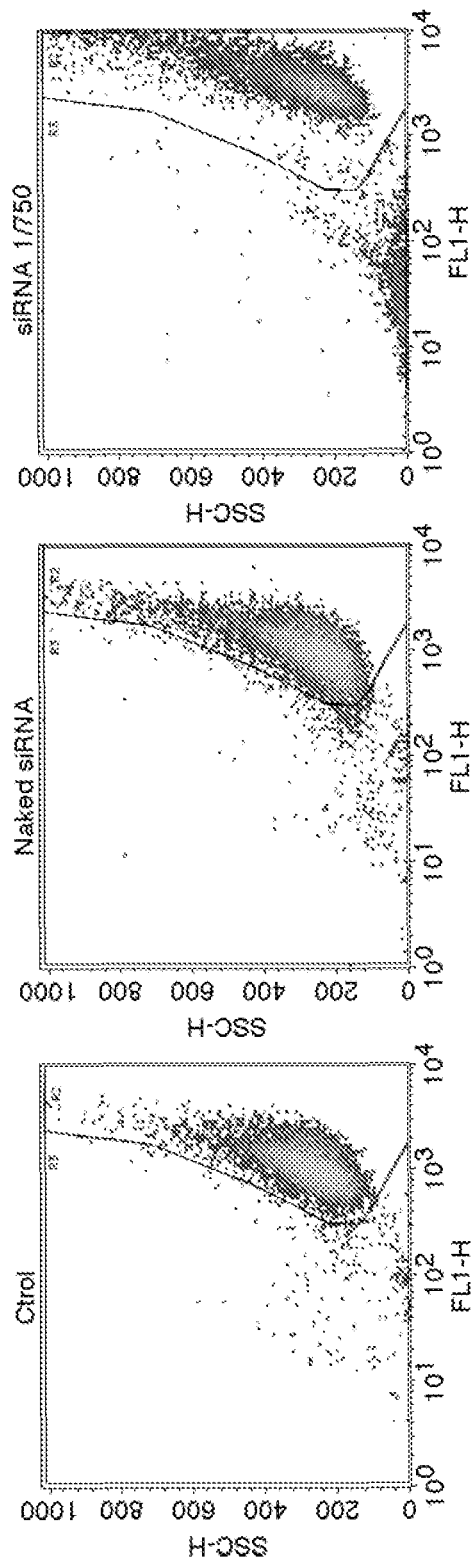
FIG. 5 is a series of schematic representations of scans showing GFP silencing in C166-GFP endothelial cells by control micelles (FIG. 5A), naked siRNA (FIG. 5B), and siRNA-S-S-PE/PEG-PE mixed micelle preparations (1:750 wt/wt) (FIG. 5C) measured by flow cytometry.

The gene silencing efficiency mediated by the siRNA delivered inside cells as siRNA-S-S-PE/PEG-PE nanosized mixed micelles (1:750 weight ratio) was studied using GFP-expressing C166 endothelial cells, in DMEM media with 10% serum. Flow cytometry data demonstrated the down-regulation of the GFP production, confirming the presence of the active free siRNA inside cells (FIG. 5C). Thus, while the naked siRNA incubated with GFP-C166 cells caused a decrease in GFP production of only about 0.5%, the same quantity of siRNA in mixed micelles resulted in almost 30% gene silencing (FIG. 6A).

E. Cell Viability

Figures 6A, 6B:
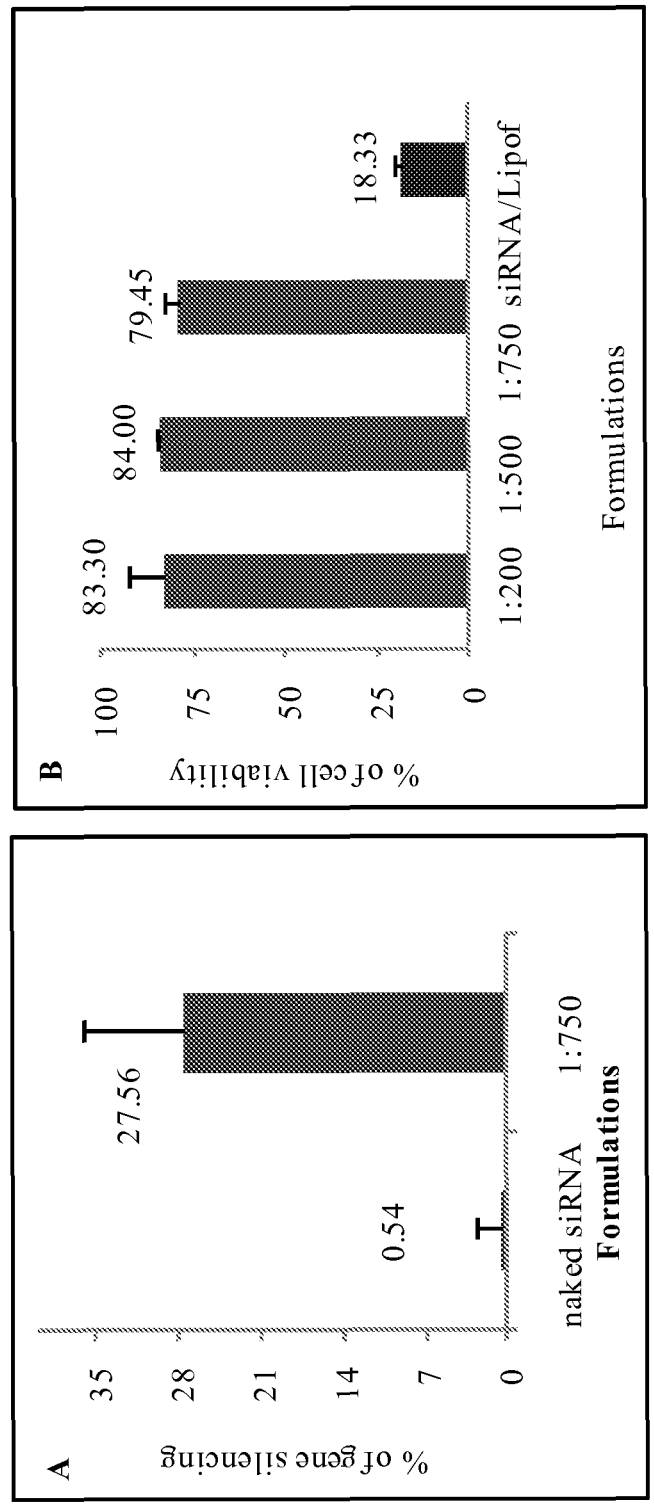
FIG. 6A is a graphic representation of GFP-silencing in GFP-C166 endothelial cells by siRNA-S-S-PE/PEG-PE mixed micelles (1:750) and siRNA/Lipofectamine as measured by flow cytometry.
FIG. 6B is a graphic representation of cell viability after a 48 h incubation with various siRNA formulations.

The comparison of cytotoxicity of siRNA-S-S-PE/PEG-PE mixed micelles with that of siRNA formulated in the standard transfection reagent, Lipofectamine, which provided a comparable level of the target gene silencing, demonstrated that the cell viability by Trypan Blue exclusion was close to 100% for all mixed micelle formulations (1:200, 1:500, and 1:750 weight ratios), whereas the viability of the cells subjected to the action of siRNA formulated with Lipofectamine (at the same quantity of siRNA) was less than 20% (FIG. 6A). Thus, the micellar formulations lacked the toxic effect associated with the use of such transfecting agents and observed with electrostatic complex-based systems.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A composition comprising:
a micelle or a liposome, the micelle or the liposome comprising:
phospholipids;
an siRNA reversibly linked to a first phospholipid, wherein the siRNA-phospholipid conjugate is part of the layer structure of the micelle or the liposome, wherein the siRNA is linked to the phospholipid by a reversible disulfide bond, and
polyethylene glycol (PEG) conjugated to an additional phospholipid of the micelle or the liposome,
wherein weight ratio of the siRNA-phospholipid conjugate to the PEG-phospholipid conjugate is about 1:200 to about 1:750.

2. The composition of claim 1, wherein the siRNA linked to the phospholipid exhibits reduced degradation by RNase after the siRNA unconjugates from the phospholipid relative to siRNA not previously linked to the first phospholipid.

3. The composition of claim 1, wherein the composition further comprises a targeting agent conjugated to the phospholipid of the micelle or the liposome.

4. The composition of claim 1, wherein the additional phospholipid in the PEG-phospholipid conjugate is different from the phospholipid in the siRNA-phospholipid conjugate.

5. The composition of claim 1, wherein the additional phospholipid in the PEG-phospholipid conjugate is the same as the phospholipid in the siRNA-phospholipid conjugate.

6. The composition of claim 1, wherein any one of the phospholipids is phosphatidylethanolamine.

7. The composition of claim 1, wherein the siRNA is linked to the phospholipid at a 3' end of the siRNA.

8. The composition of claim 1, wherein the weight ratio of the siRNA-phospholipid conjugate to the PEG-phospholipid conjugate is about 1:200.

9. The composition of claim 1, wherein the weight ratio of the siRNA-phospholipid conjugate to the PEG-phospholipid conjugate is about 1:500.

10. The composition of claim 1, wherein the weight ratio of the siRNA-phospholipid conjugate to the PEG-phospholipid conjugate is about 1:750.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 1
aannnnnnnn nnnnnnnnnn ntt                                              23

<210> SEQ ID NO 2
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
agcugacccu gaaguucaut t                                              21
```